United States Patent
Cassels et al.

(10) Patent No.: US 7,404,961 B2
(45) Date of Patent: Jul. 29, 2008

(54) PEPTIDES RESPONSIVE TO ANTIBODIES AGAINST CONSENSUS PEPTIDE OF THE CS4-CFA/I FAMILY PROTEINS

(75) Inventors: Frederick J. Cassels, Laurel, MD (US); Lawrence Loomis-Price, The Woodlands, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 326 days.

(21) Appl. No.: 10/754,642

(22) Filed: Jan. 12, 2004

(65) Prior Publication Data

US 2004/0229772 A1     Nov. 18, 2004

Related U.S. Application Data

(63) Continuation-in-part of application No. 09/801,784, filed on Mar. 9, 2001, now abandoned, which is a continuation of application No. 08/905,140, filed on Aug. 1, 1997, now abandoned.

(60) Provisional application No. 60/023,076, filed on Aug. 2, 1996.

(51) Int. Cl.
| | |
|---|---|
| A61K 39/108 | (2006.01) |
| A61K 39/02 | (2006.01) |
| A61K 39/085 | (2006.01) |
| A61K 39/00 | (2006.01) |
| A61K 38/00 | (2006.01) |

(52) U.S. Cl. ............... 424/257.1; 424/242.1; 424/241.1; 424/234.1; 424/190.1; 424/184.1; 514/2; 530/300; 530/825

(58) Field of Classification Search ............... 424/241.1, 424/194.1, 190.1, 184.1, 234.1, 242.1, 193.1, 424/831, 244.1, 257.1; 530/300, 350, 825; 514/2; 536/123.1
See application file for complete search history.

(56) References Cited

U.S. PATENT DOCUMENTS 5,914,114 A * 6/1999 Cassels ..................... 424/241.1

FOREIGN PATENT DOCUMENTS

| WO | WO 92/01703 | 2/1992 |
|---|---|---|
| WO | WO 92/14487 | 9/1992 |
| WO | WO 92/19263 | * 11/1992 |
| WO | WO 96/38171 | 12/1996 |
| WO | WO 9805687 | * 2/1998 |

OTHER PUBLICATIONS

Karjalainen et al. (1989) "Molecular Cloning and Nucleotide Sequence of the Colonization Factor Antigen I Gene of *Escherichia coli*" Infect. And Immun. 57(4):1126-1130.
Sommerfelt et al. (1992) "Genetic Relationship of Putative Colonization Factor O166 to Colonization Factor Antigen I and Coli Surface Antigen 4 of Enterotoxigenic *Escherichia coli*" Infect. And Immun. 60(9):3799-3806.
Cassels, et al. (1997) "Antibody to N-Terminal Consensus Peptide is Cross-Reactive with All Six Members of the Enterotoxigenic *E. coli* CFA/I Family" Cytokines, Cholera, and the Gut, 275-279.
Rudin and Svennerholm (1996) "Identification of a Cross-Reactive Continuous B-Cell Epitope in Enterotoxigenic *Escherichia coli* Colonization Factor Antigen I" Infection and Immunity 64(11):4508-4513.
Rudin, et al. (1994) "Monoclonal Antibodies against Enterotoxigenic *Escherichia coli* Colonization Factor Antigen I (CFA/I) that Cross-React Immunologically with Heterologous CFAs" Infection and Immunity 62(10):4339-4346.
Cassels, et al. (1992) "Analysis of *Escherichia coli* Colonization Factor Antigen I Linear B-Cell Epitopes, as Determined by Primate Responses, Following Protein Sequence Verification" Infection and Immunity 60:2174-2181.
Communication from the EPO providing search results.

* cited by examiner

*Primary Examiner*—S. Devi
(74) *Attorney, Agent, or Firm*—Elizabeth Arwine

(57) ABSTRACT

This invention relates to amino acid sequences from within a consensus peptide of the formula:

```
VEKNITVTASVDPTIDLLQADGSALPSAVALTYSPA (SEQ ID. NO: 1)
```

Eight mer peptides from within the consensus peptide were tested against an antibody raised to the consensus peptide. Studies relating to antibody raised to denatured proteins from the natural organisms producing the family of proteins were also useful and showed particular value of some sequences. A sequence of the formula ASVDPTIDLLQA (SEQ ID NO: 2) was identified thereby. An enlarge sequence of the formula TVTASVDPTIDLLQAD (SEQ ID NO: 3) is also especially interesting as are intermediate sequences such as sequences VTASVDPTIDLLQAD (SEQ ID NO: 4), TASVDPTIDLLQAD (SEQ ID NO: 5), and TASVDPTIDLLQA (SEQ ID NO: 6) as being binding sites for antibodies raised to the denatured proteins.

13 Claims, No Drawings

PEPTIDES RESPONSIVE TO ANTIBODIES AGAINST CONSENSUS PEPTIDE OF THE CS4-CFA/I FAMILY PROTEINS

CROSS REFERENCE TO RELATED APPLICATIONS

This application is a continuation-in-part of U.S. patent application Ser. No. 09/801,784, filed Mar. 9, 2001, abandoned, which was a continuation of U.S. patent application Ser. No. 08/905,140, filed Aug. 1, 1997, abandoned, and takes priority from U.S. Provisional Application No. 60/023,076, filed Aug. 2, 1996.

ACKNOWLEDGMENT OF GOVERNMENT SUPPORT

This invention was made by employees of the United States Army. The government has rights in the invention.

BACKGROUND OF THE INVENTION

1. Field of the Invention

This invention relates to amino acid sequences from within a consensus peptide of the formula:

VEKNITVTASVDPTIDLLQADGSALPSAVALTYSPA (SEQ ID NO:1)

Eight mer peptides from within the consensus peptide were tested against an antibody raised to the consensus peptide. Studies relating to antibody raised to denatured proteins from the natural organisms producing the family of proteins was also useful and showed particular value of some sequences. A sequence of the formula ASVDPTIDLLQA (SEQ ID NO:2) was identified thereby. An enlarged sequence of the formula TVTASVDPTIDLLQAD (SEQ ID NO:3) is also especially interesting as are intermediate sequences such as sequences VTASVDPTIDLLQAD (SEQ ID NO:4), TASVDPTIDLLQAD (SEQ ID NO:5), and TASVDPTIDLLQA (SEQ ID NO:6) as being binding sites for antibodies raised to the denatured proteins.

2. Description of the Related Art

The effect of E. coli in mammals is dependent on the particular strain of organism. Many beneficial E. coli are present in the intestines. Since the initial association with diarrheal illness, five categories of diarrheagenic E. coli have been identified and are presently recognized: enterotoxigenic (ETEC), enteropathogenic (EPEC), enterohemorrhagic (EHEC), enteroaggregative (EAggEC), and enteroinvasive (EIEC). These categories are grouped according to characteristic virulence properties, such as elaboration of toxins and colonization factors and/or by specific types of interactions with intestinal epithelial cells. ETEC are the most common of the diarrheagenic E. coli and pose the greatest risk to travelers. E. coli of the family CS4-CFA/I are some of the more common enterotoxigenic E. coli. There is need for vaccines which are specific against this class of E. coli that give rise to antibodies that cross-react with and cross-protect against the more common members of the CS4-CFA/I family. There are six members of this family of ETEC fimbrial proteins, CFA/I, CS1, CS2, CS4, CS17 and PCF 0166. ETEC are responsible for high infant mortality in developing countries, with an estimate that almost 800,000 deaths per year due to these organisms. These organisms also cause illness in adult travelers to regions where the disease is endemic.

Colonization factor antigens (CFA) of ETEC are important in the initial step of colonization and adherence of the bacterium to intestinal epithelia. In epidemiological studies of adults and children with diarrhea, CFA/I is found in a large percentage of morbidity attributed to ETEC. The CFA/I is present on the surfaces of bacteria in the form of pili (fimbriae), which are rigid, 7 nm diameter protein fibers composed of repeating pilin subunits. The CFA/I antigens promote mannose-resistant attachment to human brush borders with an apparent sialic acid sensitivity.

A study of proteins in E. coli belonging to the CS4-CFA/I family resulted in the finding that the N-terminal region of the protein maintains a high degree of sequence identity between members of this group. Immunological evidence shows that cross-reaction exists between members of the family CS4-CFA/I.

Cassels, et al. have identified a consensus peptide of 36 amino acids which acts as an immunogen raising antibodies against the proteins of all members of the E. coli family CS4-CFA/I. The region of the protein represented in the subunit encompasses known linear B- and T-cell epitopes of CFA/I. The consensus peptide has a high level of homology to strains bearing six different colonization factors. The consensus peptide is of the formula:

VEKNITVTASVDPTIDLLQADGSALPSAVALTYSPA (SEQ ID NO: 1)

DETAILED DESCRIPTION OF THE INVENTION

It is the purpose of this invention to identify specific epitopes that may be used to give rise to antibodies which will agglutinate all members of the E. coli family CS4-CFA/I. It is a further purpose of this invention to identify subunits of the consensus peptide previously identified by Cassels which will act as immunogens for purposes of raising antibodies against the CS4-CFA/I family proteins.

It is, furthermore, a purpose of this invention to provide kits for use in identifying all members of the CS4-CFA/I family of E. coli and antibodies to such organisms in clinical and environmental samples. The antibodies were raised to the consensus peptide of SEQ ID NO:1. (For purposes of this application, it is presumed that, unless otherwise identified, all sequences and subsequences identifed from this peptide are consecutive sequences, in accord with usual practice.)

Materials and Methods

Peptide Synthesis:

Blocks of pins for cleavable syntheses were obtained from Chiron Mimotopes U.S. Peptide synthesis was carried out according to the manufacturer's instructions using Opfp-derivatized amino acids. Peptides of length 8 with 7 overlap were manufactured in order to locate all linear epitopes in the sequence with a highest redundancy. Peptides had a linker-the amino acids Ser-Gly-Ser-Gly- (SEQ ID NO:38) and biotin covalently coupled to the N-terminus, for a total length of 12 amino acids (17 reactions, including the biotin). Peptides were cleaved from the pins using 0.1 M phosphate buffer, pH 8.0, containing 40% acetonitrile. Two peptides were made and sacrificed for amino acid analysis as proof of peptide purity. A dinitrophenol (DNP) pin was included so that the efficiency of the cleavage could be monitored spectrophotometrically.

A total of 29 peptides encompassing the entire 36 amino acid consensus peptide were synthesized as follows:

| # | Sequence | ID |
|---|---|---|
| 1. | VEKNITVT | (SEQ ID NO:7) |
| 2. | EKNITVTA | (SEQ ID NO:8) |
| 3. | KNITVTAS | (SEQ ID NO:9) |
| 4. | NITVTASV | (SEQ ID NO:10) |
| 5. | ITVTASVD | (SEQ ID NO:11) |
| 6. | TVTASVDP | (SEQ ID NO:12) |
| 7. | VTASVDPT | (SEQ ID NO:13) |
| 8. | TASVDPTI | (SEQ ID NO:14) |
| 9. | ASVDPTID | (SEQ ID NO:15) |
| 10. | SVDPTIDL | (SEQ ID NO:16) |
| 11. | VDPTIDLL | (SEQ ID NO:17) |
| 12. | DPTIDLLQ | (SEQ ID NO:18) |
| 13. | PTIDLLQA | (SEQ ID NO:19) |
| 14. | TIDLLQAD | (SEQ ID NO:20) |
| 15. | IDLLQADG | (SEQ ID NO:21) |
| 16. | DLLQADGS | (SEQ ID NO:22) |
| 17. | LLQADGSA | (SEQ ID NO:23) |
| 18. | LQADGSAL | (SEQ ID NO:24) |
| 19. | QADGSALP | (SEQ ID NO:25) |
| 20. | ADGSALPS | (SEQ ID NO:26) |
| 21. | DGSALPSA | (SEQ ID NO:27) |
| 22. | GSALPSAV | (SEQ ID NO:28) |
| 23. | SALPSAVA | (SEQ ID NO:29) |
| 24. | ALPSAVAL | (SEQ ID NO:30) |
| 25. | LPSAVALT | (SEQ ID NO:31) |
| 26. | PSAVALTY | (SEQ ID NO:32) |
| 27. | SAVALTYS | (SEQ ID NO:33) |
| 28. | AVALTYSP | (SEQ ID NO:34) |
| 29. | VALTYSPA | (SEQ ID NO:35) |

Using antibodies had been found to agglutinate *E. coli* having the CS4-CFA/I family proteins, an attempt was made to identify the binding site of response to the 36 mer consensus peptide. One monoclonal antibody raised to the consensus peptide was found to bind with all *E. coli* of the CS4-CFA/I family.

ELISA Method:

Materials:

For blocking, a composition containing 5% nonfat dry milk in PBS+0.2% sodium azide was used. Stock streptavidin (Calbiochem Corp., La Jolla, Calif.) at 1 mg/ml in water was kept frozen in aliquots for up to several months. On the day of use, the stock streptavidin was diluted in phosphate buffered saline (PBS) to provide a concentration of 5 µg/ml streptavidin. Goat F(ab')$_2$ anti-mouse, anti-rabbit and anti-human sera were labeled with alkaline phosphatase (Biosource, International, Camarillo, Calif.).

Streptavidin was plated at 5 µg/ml, 50 µl per well, and incubated over night at 4° C. Plates were then washed by hand (Nunc Immunowash 12 hand plate washer. Fisher Scientific, Pittsburgh, Pa.) three times with PBS/0.1% TWEEN 20™. Peptides were then diluted to 10 µg/ml in PBS and plated at 50-µl/well. After incubation for one hour at room temperature followed by washing, the peptides were incubated with sera diluted in blocker at appropriate concentrations (5% nonfat dry milk) for 2 hours at room temperature. After washing the wells, 50 µl of phosphatase-labeled anti-serum IgG diluted 1:1000 in blocker was added to each well and was allowed to incubate at room temperature for 1 hour. The plates were washed. The 100 µl of PNDP (p-nitrophenylphosphate) substrate, prepared according to the manufacturer's instructions, was added to each well. Results were read at 5, 15 and 60 minutes using a microtiter plate reader (UVmax™, Moelcular Devices, Sunnyvale, Calif.).

Immunization with Consensus Peptide:

The consensus peptide was conjugated to bovine serum albumin (BSA) or tetanus toxoid followed by conjugation to *Streptococcus pneumoniae* type 14 polysaccharide. When the peptide was conjugated to as indicated below, a cysteine was added at the terminal end of the peptide to provide the peptide (SEQ ID NO: 37)
CVEKNITVTASVDPTIDLLQADGSALPSAVALTYSPA The albumin or toxoid was then iodoacetylated. The peptide was mixed with the acetylated albumin or toxoid. (Sulfide bonds are thereby formed between cysteine residues providing a conjugated protein.)

Immunogenic compositions contained complete Freund's adjuvant and were administered to rabbits subcutaneously on day 1. On day 21, a booster shot was given, and on day 32, the animals were bled.

EXAMPLE 1

Rabbits were bled, then immunized on day 0 with a composition containing 280 µg peptide/BSA conjugate in Freund's complete adjuvant. On day 21, the animals were boosted with 140 µg peptide/BSA conjugate in Freund's incomplete adjuvant. Blood was drawn on day 32. The interaction of antibodies raised against the specific antigens of the denatured proteins of the various strains was studied by comparing interaction of serum from the animals obtained on day 0 with response on to serum from the animals obtained on day 32 by Western blot. In all instances, the Western blot was negative for reaction with serum obtained on day 0. The Western blot data on interaction of immune serum collected on day 32 with the denatured proteins is given below with 0 being no reaction and 4 being a strong reaction:

| Titer | 1:50 | 1:500 | 1:5000 | 1:50000 |
|---|---|---|---|---|
| CS1 | 4 | 4 | 4 | 4 |
| CS2 | 4 | 4 | 4 | |
| CS4 | 4 | 4 | 3 | 2 |
| CS17 | 4 | 3 | 2 | 0.5 |
| 0166 | 4 | 1 | 3 | |
| CFA/1 | 4 | 3 | 2 | |

EXAMPLE 2

An immunogenic composition is prepared containing 2800 µg/ml of a conjugate of a peptide of the formula:

VEKNITVTASVDPTIDLLQADGSALPSAVALTYSPA (SEQ ID NO:1)

bound to BSA through a cysteine in complete Freund's reagent.

EXAMPLE 3

A immunogenic composition is prepared containing 4000 µg/ml of a peptide of the formula:

VEKNITVTASVDPTIDLLQADGSALPSAVALTYSPA (SEQ ID NO: 1)

in complete Freund's adjuvant.

EXAMPLE 4

Rabbits were given a composition containing 400 µg peptide of the formula: VEKNITVTASVDPTIDLLQADGSALPSAVALTYSPA (SEQ ID NO:1) in complete Freund's adjuvant. The response was evaluated as in Example 2:

| Titer | 1:50 | 1:500 | 1:5000 | 1:50000 |
|---|---|---|---|---|
| CS1 | 4 | 4 | 2 | 1 |
| CS2 |  |  |  |  |
| CS4 | 2 | 0 | 0 | 0 |
| CS17 | 2 | 0 | 0 | 0 |
| 0166 | 4 | 2 |  |  |
| CFA/I |  |  |  |  |

EXAMPLE 5

The same study was done comparing antibodies raised to denatured proteins of PCF 0166.

| Titer | 1:1000 | 1:10000 | 1:100000 |
|---|---|---|---|
| CS1 | 3 | 0.5 | 0 |
| CS2 | 2 | 1 | 0 |
| CS4 | 2 | 0.5 | 0.5 |
| CS17 | 3 | 0.5 | 0 |
| 0166 | 4 | 3 | 1 |
| CFA/I | 3 | 0.5 | 0 |

EXAMPLE 6

Effect of antibody raised to whole CS2 protein was studied in the manner of example 5.

| Titer | 1:1000 | 1:10000 | 1:100000 |
|---|---|---|---|
| CS1 | 4 | 3 | 0.5 |
| CS2 | 2 | 2 | 0 |
| CS4 | 3 | 1 | 0 |
| CS17 | 3 | 1 | 0 |
| 0166 | 4 | 1 | 0 |
| CFA/I | 3 | 0 | 0 |

EXAMPLE 7

Studies were conducted to determine whether antibodies raised to the peptide would cause agglutination of whole bacteria of various strains. Antibody responses to three preparations of consensus peptide antigen were used to immunize the rabbits were compared: 1) peptide conjugated to bovine serum albumin (aPepBS), 2) free peptide (aPepFr) and 3) peptide conjugated to tetanus toxoid and *S. pneumoniae* T14 (aPepTT). The tetanus toxoid was conjugated to the peptide using the described above for conjugation to BSA. The three preparations were used to immunize two animals each. The serum was then contacted with whole bacteria and the slides were inspected for agglutination of the bacteria.

| CF | aPepBSA | aPepFr | aPepTT |
|---|---|---|---|
| CS1 | 1/2 | 0/2 | 1/2 |
| CS2 | 2/2 | 0/2 | 2/2 |
| CS4 | 0/2 | 0/2 | 0/2 |
| CS17 | 0/2 | 0/2 | 0/2 |
| 0166 | 1/2 | 0/2 | 2/2 |
| CFA/1 | 1/2 | 0/2 | 2/2 |

In view of the test data, it is seen that the data indicates that consensus proteins can give rise to antibodies that react to denatured protein and cause agglutination of more than one strain of *E. coli* of the CS4-CFA/I family. However, it is also seen that conjugation to a larger molecule provides improved properties to the peptides for purposes of raising antibodies to the whole bacteria and the proteins of these organisms.

Antibodies from the rabbits were then tested against the specific 8-mer peptides obtained from SEQ ID NO:1 in the manner disclosed above to determine the binding sites of the antibodies in the sera with the consensus peptide.

It appeared, under this method of testing, that the most reactive peptides are those containing peptides 2, 3, 4, 5, 8, 9, 10, 11, 12, 13, 14, 23, 24, 25, 26, 27, 28, and 29 of the formulas: EKNITVTA (SEQ ID NO:8), KNITVTAS (SEQ ID NO:9), NITVTASV (SEQ ID NO:10), ITVTASVD (SEQ ID NO:11), TASVDPTI (SEQ ID NO:14), ASVDPTID (SEQ ID NO:15), SVDPTIDL (SEQ ID NO:16), VDPTIDLL (SEQ ID NO:17), DPTIDLLQ (SEQ ID NO:18), PTIDLLQA (SEQ ID NO:19), SALPSAVA (SEQ ID NO:29), ALPSAVAL (SEQ ID NO:30), LPSAVALT (SEQ ID NO:31), PSAVALTY (SEQ ID NO:32), SAVALTYS (SEQ ID NO:33), AVALTYSP (SEQ ID NO:34), and VALTYSPA (SEQ ID NO:35). In view of this data, the epitopes containing these peptides would be preferred for use in reaction with antibodies raised to the consensus peptide. Epitopes containing the peptides ASVDPTID (SEQ ID NO:15), SVDPTIDL (SEQ ID NO:16), VDPTIDLL (SEQ ID NO:17), DPTIDLLQ (SEQ ID NO:18), PTIDLLQA (SEQ ID NO:19), PSAVALTY (SEQ ID NO:32), SAVALTYS (SEQ ID NO:33), and AVALTYSP (SEQ ID NO:34) were more reliably interactive with the antibodies raised to the consensus peptide. It is also likely that the addition of a proline to either one or both ends of any peptide which does not end with that amino acid would be expected to increase binding ability. The peptide of the formula SAVAL-TYS (SEQ ID NO:33) especially when bounded by a proline to provide PSAVALTYSP (SEQ ID NO:36) is a preferred peptide.

Application of PEPSCAN Data to 8 Mer Units:

Using this method, other sequences including that of the formula ASVDPTIDLLQA (SEQ ID NO:2) were identified. An enlarged sequence of the formula TVTASVDP-TIDLLQAD (SEQ ID NO:3) is also especially interesting as are intermediate sequences such as sequences VTASVDP-TIDLLQAD (SEQ ID NO:4), TASVDPTIDLLQAD (SEQ ID NO:5), and TASVDPTIDLLQA (SEQ ID NO:6) as being binding sites for antibodies raised to the denatured proteins.

Procedure for Obtaining Antibody to Denature Subunits:

Partially to fully purified colonization factor (40% to 100% pure) was run on SDS-PAGE gel (5-15 µg/lane of 10 comb gel (precast 10 comb, 1 mm thickness, Tris-tricene gel from Novex, San Diego, Calif.), for primary immunization run 9 lanes for each rabbit (45-135 µg CF protein with ½ the amount used in the primary immunization used as a booster). The gel was stained with 0.5% COOMASSIE BLUE™ (Bio-Rad, Richmond, Calif.) in water for 1 hour, then destained with multiple changes of water for 60-90 minutes. The colonization factor bands were excised with a scalpel and the excess gel trimmed. The bands were stored at −20° C. until use.

Immunization:

After removal from freezer, the gel slices were transferred to a glass tissue homogenizer using a teflon pestle with grooves at the tip. The slices were ground with 0.3 ml phosphate buffered saline (PBS). The drill was run to homogenize the gel for 30 to 45 seconds. (In the instant case, a pestle with a shaft of steel was used which allowed placement of the pestle into the chuck of the hand-held drill.)

The homogenate was transferred to 16 mm×150 mm test tubes with disposable plastic transfer pipet. The pestle and homogenizer vessel was rinsed repeatedly with PBS and the contents transferred to the 16×150 test tube until a volume of 1.2 ml was obtained.

The sample obtained above was placed in a vortex mixer and vortexed on high. Freund's adjuvant 1.2 ml was added. (Complete Freund's was used for the primary immunization, while incomplete Freund's was used for the boost.) The composition was vortexed until a thick emulsion of almost a butter consistency was obtained (12-20 minutes).

A preimmune serum was obtained on all animals, which were then immunized with the 1 ml of the emulsion subcutaneously at 4-6 spots on the shoulders and rump. The animals were boosted three weeks later, then bleed 10 days after the booster shots.

The 8-mer peptides were exposed to the serum of the animals and the samples examined by means disclosed above to determine whether binding had occurred. The data is shown below.

Testing with antibodies indicated those epitopes which bound to the antibodies. As a result, it was possible to identify those epitopes which were most likely to bind to antibodies in a serum sample.

Antibody to:
Rabbit number followed by pins (8-aa peptide) recognized by serum.

| CFA/I | |
|---|---|
| 1078 | 13, 14 |
| 1079 | 11, 13, 14 |
| CS1 | |
| 1089 | 3, 4, 10, 11, 12, 13, 18, 19, 20, 21, 28, 29 |
| 1090 | 4, 6, 7, 8, 9, 10, 11, 12, 13, 18, 19, 20, 21, 22, 23, 23, 24, 26, 27, 28, 29 |
| CS2 | |
| 1076 | 7, 8, 9, 10, 11, 12 |
| 1077 | 7, 8, 9, 10, 11, 24 |
| CS4 | |
| 938 | 8, 9, 10, 11, 12, 13, 26 |
| 940 | 1, 2, 3, 10, 11, 12, 13, 14, 22, 24, 25 |
| CS17 | |
| 1080 | 2, 3, 4, |
| 1084 | 1, 6, 7, 8, 9 |
| 0166 upper | |
| 934 | 12, 13, 14 |
| 1081 | 9, 10, 11, 12, 13, 15, 16, 17 |
| 0166 lower | |
| 1082 | 9, 11, 12, 13, 14 |
| 1083 | 2, 3, 12, 13 |

From the above data, units of the consensus peptide of SEQ ID NO:1 which could be expected to interact with nearly all antibodies arising in response to the natural organisms were identified. Such a peptide encompasses all the amino acids of SEQ ID NO:12 through SEQ ID NO:20, namely: TVTAS-VDPTIDLLQAD (SEQ ID NO:3). The sequence may be shortened somewhat with deletion of any or all of the first three amino acids and the last amino acid, but should contain the amino sequences ASVDPTIDLLQA (SEQ ID NO:2) for purposes of retaining activity against the target class of organisms. Peptides containing these sequences should react with most antibodies of the natural organisms producing CS4-CFA/I family of proteins and may be used to determine whether an individual animal has antibodies to ETEC E. coli. These sequences, as well as the larger consensus peptide and the other 8-mer peptides disclosed herein may be used to elicit antibodies to the natural organisms producing CS4-CFA/I family proteins.

The peptides of the invention are useful for immunization to raise antibodies to the organisms producing the CS4-CFA/I family of proteins. Particularly preferred sequences are those containing SEQ ID NO:2, SEQ ID NO:3, SEQ ID NO:33 and SEQ ID NO:36 since these epitopes bind to the effective antibodies. For purposes of immunization, it is preferred that the peptides containing these sequences from these preferred sequences contain at least 16 amino acids. The peptides of the invention may be administered in pharmaceutically acceptable carriers for administration by usual means known in the art, including subcutaneously, intradramally, orally or nasally. Adjuvants known in the art may be used in such carriers. The immunogenic peptides may be administered as a primary dose with second and third dosings used as boosters, in accord with the teachings herein.

The antibodies raised to the peptides are useful for identifying members of the CS4-CFA/I family in cultures. Assay kits containing the antibodies may be prepared and may contain, in addition, agents for tagging for facilitated identification of the antibody/antigen complex. Such tags include radioactive isotopes, fluorescing agents and colorometric indicators. Such agents may be attached to solid supports. For example, an ELISA test kit system may be used to identify the antibody/antigen complex.

Compositions containing the antibodies raised in accord with the teachings herein may be prepared using a carrier appropriate for addition to a growth media. Saline and other buffered solutions known in the art are appropriate as carriers for the antibodies.

Antibodies raised to the sequences of the invention may be prepared in pharmaceutically acceptable carrier solutions and may be administered to the infected area to agglutinate the bacteria bearing CS4-CFA/I proteins. Administration would provide means for the compositions to contact the organisms. For example, the compositions could be administered orally in capsules which protect the antibody from destruction in the stomach and duodenum. The compositions are appropriate for use both for short-term prophylaxis and for treatment of ETEC *E. coli* infections by administration of an ETEC *E. coli* agglutinating effective amount of the pharmaceutical composition.

For use in vaccine compositions sequences containing at least one peptide of at least 8 amino acids but no more than 30 amino acids having sequences of a concensus peptide of SEQ ID NO:1 or SEQ ID NO:2, said peptides having sequences chosen from: EKNITVTA (SEQ ID NO:8), KNITVTAS (SEQ ID NO:9), NITVTASV (SEQ ID NO:10), ITVTASVD (SEQ ID NO:11), TASVDPTI (SEQ ID NO:14), ASVDPTID (SEQ ID NO:15), SVDPTIDL (SEQ ID NO:16), VDPTIDLL (SEQ ID NO:17), DPTIDLLQ (SEQ ID NO:18), PTIDLLQA (SEQ ID NO:19), SALPSAVA (SEQ ID NO:29), ALPSAVAL (SEQ ID NO:30), LPSAVALT (SEQ ID NO:31), PSAVALTY (SEQ ID NO:32), SAVALTYS (SEQ ID NO:33), AVALTYSP (SEQ ID NO:34), and VALTYSPA (SEQ ID NO:35), PSAVALTYSP (SEQ ID NO:36), TVTASVDPTIDLLQAD (SEQ ID NO:3), and ASVDPTIDLLQA (SEQ ID NO:2) may be used. It is preferred that such peptides have at least 16 amino acids. The compositions for use as immunogens may also contain adjuvants used in the art.

What is claim is:

1. An isolated peptide selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NQ: 26, SEQ ID NO: 27, SEQ ID NO: 28, SEQ ID NO: 29, SEQ ID NO: 30, SEQ ID NO: 31, SEQ ID NO: 32, SEQ ID NO: 33, and SEQ ID NO: 35.

2. The isolated peptide of claim 1, wherein the peptide has a proline bound to one of the ends.

3. The isolated peptide of claim 1, wherein the SEQ ID NO: 33 has a proline bound at both ends.

4. A composition comprising the peptide according to claim 1 and a pharmaceutically acceptable carrier.

5. The composition of claim 4, wherein the composition further comprises an adjuvant.

6. An isolated peptide selected from the group consisting of SEQ ID NO: 12, SEQ ID NO: 25 and SEQ ID NO: 34.

7. A composition comprising the peptide according to claim 6 and a pharmaceutically acceptable carrier.

8. The composition of claim 7, and further comprising an adjuvant.

9. An isolated 16 to 30 amino acid-long peptide containing an amino acid sequence selected from the group consisting of SEQ ID NO: 2, SEQ ID NO: 3, SEQ ID NO: 33 and SEQ ID NO: 36.

10. A composition comprising the isolated peptide of claim 9.

11. A method of immunizing a susceptible host comprising administering an immunizing effective amount of the composition of claim 4.

12. A method of immunizing a susceptible host comprising administering an immunizing effective amount of the composition of claim 7.

13. A method of immunizing a susceptible host comprising administering an immunizing effective amount of the composition of claim 10.

* * * * *

SEQUENCE LISTING

```
<160> NUMBER OF SEQ ID NOS: 38

<210> SEQ ID NO 1
<211> LENGTH: 36
<212> TYPE: PRT
<213> ORGANISM: Escherichia coli

<400> SEQUENCE: 1

Val Glu Lys Asn Ile Thr Val Thr Ala Ser Val Asp Pro Thr Ile Asp
1               5                   10                  15

Leu Leu Gln Ala Asp Gly Ser Ala Leu Pro Ser Ala Val Ala Leu Thr
            20                  25                  30

Tyr Ser Pro Ala
        35

<210> SEQ ID NO 2
<211> LENGTH: 12
<212> TYPE: PRT
<213> ORGANISM: Escherichia coli

<400> SEQUENCE: 2

Ala Ser Val Asp Pro Thr Ile Asp Leu Leu Gln Ala
1               5                   10

<210> SEQ ID NO 3
<211> LENGTH: 16
<212> TYPE: PRT
<213> ORGANISM: Escherichia coli

<400> SEQUENCE: 3

Thr Val Thr Ala Ser Val Asp Pro Thr Ile Asp Leu Leu Gln Ala Asp
1               5                   10                  15

<210> SEQ ID NO 4
<211> LENGTH: 15
<212> TYPE: PRT
<213> ORGANISM: Escherichia coli

<400> SEQUENCE: 4

Val Thr Ala Ser Val Asp Pro Thr Ile Asp Leu Leu Gln Ala Asp
1               5                   10                  15
```

```
<210> SEQ ID NO 5
<211> LENGTH: 14
<212> TYPE: PRT
<213> ORGANISM: Escherichia coli

<400> SEQUENCE: 5

Thr Ala Ser Val Asp Pro Thr Ile Asp Leu Leu Gln Ala Asp
1               5                   10

<210> SEQ ID NO 6
<211> LENGTH: 13
<212> TYPE: PRT
<213> ORGANISM: Escherichia coli

<400> SEQUENCE: 6

Thr Ala Ser Val Asp Pro Thr Ile Asp Leu Leu Gln Ala
1               5                   10

<210> SEQ ID NO 7
<211> LENGTH: 8
<212> TYPE: PRT
<213> ORGANISM: Escherichia coli

<400> SEQUENCE: 7

Val Glu Lys Asn Ile Thr Val Thr
1               5

<210> SEQ ID NO 8
<211> LENGTH: 8
<212> TYPE: PRT
<213> ORGANISM: Escherichia coli

<400> SEQUENCE: 8

Glu Lys Asn Ile Thr Val Thr Ala
1               5

<210> SEQ ID NO 9
<211> LENGTH: 8
<212> TYPE: PRT
<213> ORGANISM: Escherichia coli

<400> SEQUENCE: 9

Lys Asn Ile Thr Val Thr Ala Ser
1               5

<210> SEQ ID NO 10
<211> LENGTH: 8
<212> TYPE: PRT
<213> ORGANISM: Escherichia coli

<400> SEQUENCE: 10

Asn Ile Thr Val Thr Ala Ser Val
1               5

<210> SEQ ID NO 11
<211> LENGTH: 8
<212> TYPE: PRT
<213> ORGANISM: Escherichia coli

<400> SEQUENCE: 11

Ile Thr Val Thr Ala Ser Val Asp
1               5
```

```
<210> SEQ ID NO 12
<211> LENGTH: 8
<212> TYPE: PRT
<213> ORGANISM: Escherichia coli

<400> SEQUENCE: 12

Thr Val Thr Ala Ser Val Asp Pro
1               5

<210> SEQ ID NO 13
<211> LENGTH: 8
<212> TYPE: PRT
<213> ORGANISM: Escherichia coli

<400> SEQUENCE: 13

Val Thr Ala Ser Val Asp Pro Thr
1               5

<210> SEQ ID NO 14
<211> LENGTH: 8
<212> TYPE: PRT
<213> ORGANISM: Escherichia coli

<400> SEQUENCE: 14

Thr Ala Ser Val Asp Pro Thr Ile
1               5

<210> SEQ ID NO 15
<211> LENGTH: 8
<212> TYPE: PRT
<213> ORGANISM: Escherichia coli

<400> SEQUENCE: 15

Ala Ser Val Asp Pro Thr Ile Asp
1               5

<210> SEQ ID NO 16
<211> LENGTH: 8
<212> TYPE: PRT
<213> ORGANISM: Escherichia coli

<400> SEQUENCE: 16

Ser Val Asp Pro Thr Ile Asp Leu
1               5

<210> SEQ ID NO 17
<211> LENGTH: 8
<212> TYPE: PRT
<213> ORGANISM: Escherichia coli

<400> SEQUENCE: 17

Val Asp Pro Thr Ile Asp Leu Leu
1               5

<210> SEQ ID NO 18
<211> LENGTH: 8
<212> TYPE: PRT
<213> ORGANISM: Escherichia coli

<400> SEQUENCE: 18

Asp Pro Thr Ile Asp Leu Leu Gln
1               5

<210> SEQ ID NO 19
<211> LENGTH: 8
```

```
<212> TYPE: PRT
<213> ORGANISM: Escherichia coli

<400> SEQUENCE: 19

Pro Thr Ile Asp Leu Leu Gln Ala
1               5

<210> SEQ ID NO 20
<211> LENGTH: 8
<212> TYPE: PRT
<213> ORGANISM: Escherichia coli

<400> SEQUENCE: 20

Thr Ile Asp Leu Leu Gln Ala Asp
1               5

<210> SEQ ID NO 21
<211> LENGTH: 8
<212> TYPE: PRT
<213> ORGANISM: Escherichia coli

<400> SEQUENCE: 21

Ile Asp Leu Leu Gln Ala Asp Gly
1               5

<210> SEQ ID NO 22
<211> LENGTH: 8
<212> TYPE: PRT
<213> ORGANISM: Escherichia coli

<400> SEQUENCE: 22

Asp Leu Leu Gln Ala Asp Gly Ser
1               5

<210> SEQ ID NO 23
<211> LENGTH: 8
<212> TYPE: PRT
<213> ORGANISM: Escherichia coli

<400> SEQUENCE: 23

Leu Leu Gln Ala Asp Gly Ser Ala
1               5

<210> SEQ ID NO 24
<211> LENGTH: 8
<212> TYPE: PRT
<213> ORGANISM: Escherichia coli

<400> SEQUENCE: 24

Leu Gln Ala Asp Gly Ser Ala Leu
1               5

<210> SEQ ID NO 25
<211> LENGTH: 8
<212> TYPE: PRT
<213> ORGANISM: Escherichia coli

<400> SEQUENCE: 25

Gln Ala Asp Gly Ser Ala Leu Pro
1               5

<210> SEQ ID NO 26
<211> LENGTH: 8
<212> TYPE: PRT
<213> ORGANISM: Escherichia coli
```

-continued

```
<400> SEQUENCE: 26

Ala Asp Gly Ser Ala Leu Pro Ser
1               5

<210> SEQ ID NO 27
<211> LENGTH: 8
<212> TYPE: PRT
<213> ORGANISM: Escherichia coli

<400> SEQUENCE: 27

Asp Gly Ser Ala Leu Pro Ser Ala
1               5

<210> SEQ ID NO 28
<211> LENGTH: 8
<212> TYPE: PRT
<213> ORGANISM: Escherichia coli

<400> SEQUENCE: 28

Gly Ser Ala Leu Pro Ser Ala Val
1               5

<210> SEQ ID NO 29
<211> LENGTH: 8
<212> TYPE: PRT
<213> ORGANISM: Escherichia coli

<400> SEQUENCE: 29

Ser Ala Leu Pro Ser Ala Val Ala
1               5

<210> SEQ ID NO 30
<211> LENGTH: 8
<212> TYPE: PRT
<213> ORGANISM: Escherichia coli

<400> SEQUENCE: 30

Ala Leu Pro Ser Ala Val Ala Leu
1               5

<210> SEQ ID NO 31
<211> LENGTH: 8
<212> TYPE: PRT
<213> ORGANISM: Escherichia coli

<400> SEQUENCE: 31

Leu Pro Ser Ala Val Ala Leu Thr
1               5

<210> SEQ ID NO 32
<211> LENGTH: 8
<212> TYPE: PRT
<213> ORGANISM: Escherichia coli

<400> SEQUENCE: 32

Pro Ser Ala Val Ala Leu Thr Tyr
1               5

<210> SEQ ID NO 33
<211> LENGTH: 8
<212> TYPE: PRT
<213> ORGANISM: Escherichia coli

<400> SEQUENCE: 33
```

```
Ser Ala Val Ala Leu Thr Tyr Ser
1               5

<210> SEQ ID NO 34
<211> LENGTH: 8
<212> TYPE: PRT
<213> ORGANISM: Escherichia coli

<400> SEQUENCE: 34

Ala Val Ala Leu Thr Tyr Ser Pro
1               5

<210> SEQ ID NO 35
<211> LENGTH: 8
<212> TYPE: PRT
<213> ORGANISM: Escherichia coli

<400> SEQUENCE: 35

Val Ala Leu Thr Tyr Ser Pro Ala
1               5

<210> SEQ ID NO 36
<211> LENGTH: 10
<212> TYPE: PRT
<213> ORGANISM: Escherichia coli

<400> SEQUENCE: 36

Pro Ser Ala Val Ala Leu Thr Tyr Ser Pro
1               5                   10

<210> SEQ ID NO 37
<211> LENGTH: 37
<212> TYPE: PRT
<213> ORGANISM: Escherichia coli

<400> SEQUENCE: 37

Cys Val Glu Lys Asn Ile Thr Val Thr Ala Ser Val Asp Pro Thr Ile
1               5                   10                  15

Asp Leu Leu Gln Ala Asp Gly Ser Ala Leu Pro Ser Ala Val Ala Leu
            20                  25                  30

Thr Tyr Ser Pro Ala
        35

<210> SEQ ID NO 38
<211> LENGTH: 4
<212> TYPE: PRT
<213> ORGANISM: Escherichia coli

<400> SEQUENCE: 38

Ser Gly Ser Gly
1
```